(12) United States Patent
Ruhland et al.

(10) Patent No.: US 9,353,073 B2
(45) Date of Patent: May 31, 2016

(54) VORTIOXETINE MANUFACTURING PROCESS

(71) Applicant: H. Lundbeck A/S, Valby (DK)

(72) Inventors: Thomas Ruhland, Roskilde (DK); Kim Lasse Christensen, Slagelse (DK)

(73) Assignee: H. Lundbeck A/S, Valby (DK)

( * ) Notice: Subject to any disclaimer, the term of this patent is extended or adjusted under 35 U.S.C. 154(b) by 0 days.

(21) Appl. No.: 14/767,350

(22) PCT Filed: Feb. 20, 2014

(86) PCT No.: PCT/EP2014/053313
§ 371 (c)(1),
(2) Date: Aug. 12, 2015

(87) PCT Pub. No.: WO2014/128207
PCT Pub. Date: Aug. 28, 2014

(65) Prior Publication Data
US 2016/0009670 A1  Jan. 14, 2016

Related U.S. Application Data

(60) Provisional application No. 61/767,883, filed on Feb. 22, 2013.

(30) Foreign Application Priority Data

Feb. 22, 2013  (DK) ................. 2013 00104

(51) Int. Cl.
*C07D 295/096* (2006.01)
*C07F 15/02* (2006.01)

(52) U.S. Cl.
CPC ............ *C07D 295/096* (2013.01); *C07F 15/02* (2013.01)

(58) Field of Classification Search
CPC .................................................. C07D 295/096
See application file for complete search history.

(56) References Cited

FOREIGN PATENT DOCUMENTS

WO    03029232 A1    4/2003

OTHER PUBLICATIONS

International Search Report for PCT/EP2014/053313 dated Mar. 20, 2014. 2 pages.

*Primary Examiner* — Bruck Kifle
(74) *Attorney, Agent, or Firm* — Fish & Richardson P.C.

(57) ABSTRACT

A process for the manufacture of vortioxetine is provided in which a compound of formula I, formula I is reacted with optionally substituted piperazine and 2,4-dimethylthiophenol(ate) followed by de-cmplexation.

12 Claims, 1 Drawing Sheet

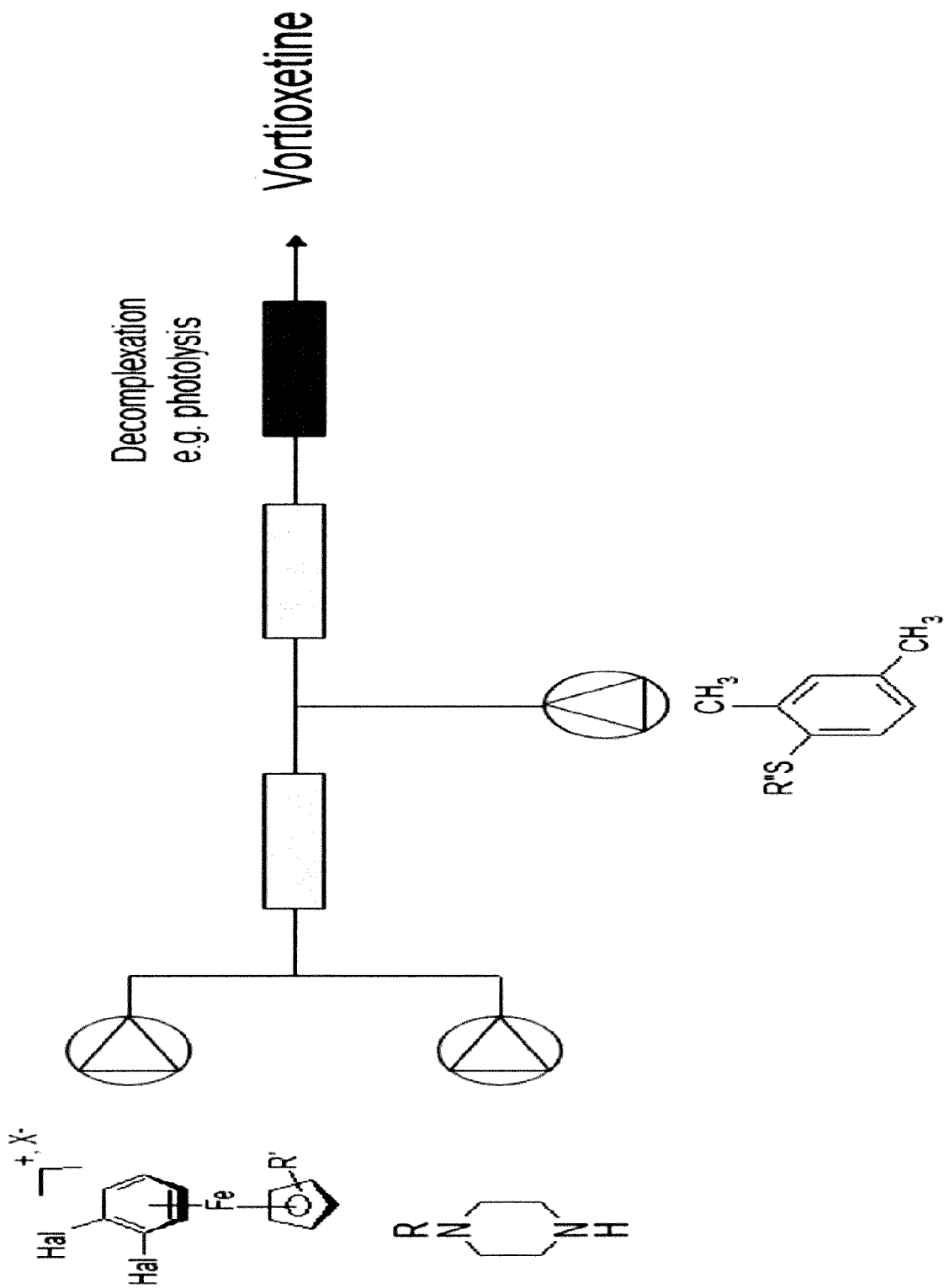

VORTIOXETINE MANUFACTURING PROCESS

CROSS REFERENCE TO PRIOR APPLICATIONS

This is a U.S. National Phase application under U.S.C. §371 of International Patent Application No. PCT/EP2014/053313, filed Feb. 20, 2014, which claims the benefit of U.S. Provisional Application No. 61/767,883, filed Feb. 22, 2013 and DK Application No. PA201300104, filed Feb. 22, 2013. The International Application was published on Aug. 28, 2014 as International Publication No. WO/2014/128207 under PCT Article 21(3). The contents of the above applications are incorporated herein in their entirety.

FIELD OF INVENTION

The present invention relates to a process for the manufacture of 1-[2-(2,4-dimethylphenylsulfanyl)phenyl]-piperazine or pharmaceutically acceptable salts thereof.

BACKGROUND OF THE INVENTION

International patent applications including WO 03/029232 and WO 2007/144005 disclose the compound 1-[2-(2,4-dimethyl-phenylsulfanyl)-phenyl]-piperazine and pharmaceutically acceptable salts thereof. WHO has since published that vortioxetine is the recommended International Non-proprietary Name (INN) for 1-[2-(2,4-dimethyl-phenylsulfanyl)-phenyl]-piperazine. Vortioxetine was formerly referred to in the literature as Lu AA21004. FDA and EMA have since approved vortioxetine for the treatment of depression under the trade name Brintellix™.

Vortioxetine is a 5-HT$_3$, 5-HT$_7$, and 5-HT$_{1D}$ receptor antagonist, 5-HT$_{1B}$ receptor partial agonist, 5-HT$_{1A}$ receptor agonist and inhibitor of the 5-HT transporter. Additionally, vortioxetine has demonstrated to enhance the levels of the neurotransmitters serotonin, noradrenalin, dopamine, acetylcholine and histamine in specific areas of the brain. All of these activities are considered to be of clinical relevance and potentially involved in the mechanism of action of the compound [*J. Med. Chem.*, 54, 3206-3221, 2011; *Eur. Neuropshycopharmacol.*, 18(suppl 4), S321, 2008; *Eur. Neuropshycopharmacol.*, 21(suppl 4), S407-408, 2011; *Int. J. Psychiatry Clin Pract.* 5, 47, 2012].

Vortioxetine has in clinical trials shown to be a safe and efficacious treatment for depression. A paper reporting the results from a proof-of-concept study to evaluate the efficacy and tolerability of the compound in patients with major depressive disorder (MDD) authored by Alvares et at was made available on-line by *Int. J. Neuropsychopharm.* 18 Jul. 2011. The results from the six weeks, randomised, placebo-controlled study with approximately 100 patients in each arm show that vortioxetine separates significantly from placebo in the treatment of depressive and anxious symptoms in patients with MDD. It is also reported that no clinically relevant changes were seen in the clinical laboratory results, vital signs, weight, or ECG parameters. Results from a long-term study also show that vortioxetine is effective in preventing relapse in patients suffering from MDD [*Eur. Neuropsychopharmacol.* 21(suppl 3), S396-397, 2011]. A study in elderly depressed patients reported in *Int. Clin. Psychopharm.*, 27, 215-227, 2012 shows that vortioxetine may be used to treat cognitive dysfunctions.

The manufacturing process used to prepare vortioxetine disclosed in WO 03/029232 is based on solid-phase synthesis and exploits di-arene iron-assisted nucleophilic aromatic substitution reactions in a multistep process. In summary, 4-[piperazine-1-yl]carbonyloxymethyl]phenoxymethyl polystyrene was reacted with a di-arene iron salt, i.e. η$^6$-1,2-dichlorobenzene-η$^5$-cyclopentadienyliron(II) hexafluorophosphate followed by isolation and washing of the resin and further reaction with 2,4-dimethylthiophenol. Finally, the thus obtained resin was treated with 1,10-phenanthroline and light to de-complex cyclopentadienyliron. The overall yield was low, only 17%. A similar process is disclosed in WO 01/49678 wherein phenoxyphenylpiperazines are prepared as intermediates.

Di-arene iron compounds have been known for long time, exemplified by ferrocene which consists of two pentadienyl rings bound to iron in a sandwich structure. These compounds have proved to be useful tools in the preparation of e.g. heterocyclic compounds. As an example, Pearson et al in *J. Org. Chem.* 61, 1297-1305, 1996 disclose displacement of chloro atoms from 1,4-dichlorobenzene-cyclopentadienyl-iron (II) by cyclic secondary amines, e.g. piperazine. Interestingly, this reaction results in a symmetric displacement, i.e. displacement of both chloro atoms from the benzene moiety. Sutherland et al in *J. Heterocyclic Chem.*, 19, 801-803, 1982 disclose that both chloro atoms in 1,2-dichlorobenzene-cyclopentadienyl-iron(II) are displaced by substituted 1,2-dithiophenol to obtain the corresponding thiaanthrenes. Pearson et al [*J. Org Chem.*, 59, 4561-4570, 1994] disclose the use of 1-4-dichlorobenzene-cyclopentadienyl-iron(II) hexafluorophosphate in the manufacture of asymmetric compounds in which the two chloro atoms are substituted by phenoxy and morpholine, respectively. Notably, the two substitutions require very different reaction conditions and isolation of the intermediate, mono-substituted compound was required. Ruhland et al in *J. Org. Chem.*, 67, 5257-5268, 2002 disclose synthesis of 1,2-disubstituted benzenes where selective substitution with different substitutions of the chemically identical chloro atoms is achieved via cyclopentadienyl activation in solid phase.

Solid-phase chemistry is not feasible for pharmaceutical production involving manufacturing in ton-scale. The massive handling of resins that would be required and the costs associated are prohibitive. Additionally, the low yield obtained for votioxetine (only 17%) makes this manufacturing route unattractive.

Large scale manufacturing of vortioxetine has been disclosed in WO 2007/144005 and WO 2010/094285. Piperazine, 2,4-dimethylthiophenol and 1,2-dihalogenbenzene are mixed e.g. in toluene together with a palladium catalyst to afford vortioxetine. Although this reaction provides high yield and can be handled in large scale, it requires the use of an expensive catalyst, i.e. palladium. Moreover, the reaction conditions are harsh employing elevated temperatures to obtain a satisfactory result, i.e. reflux temperatures or 80-120° C. and the use of strong base.

The present invention provides a manufacturing process for vortioxetine which uses inexpensive starting materials, which can be run at mild conditions and which gives high yields.

SUMMARY OF THE INVENTION

The present inventors have found that 1-[2-(2,4-dimethyl-phenylsulfanyl)-phenyl]-piperazine (vortioxetine) or pharmaceutically acceptable salts thereof can be prepared in a reaction in which a suitable di-arene iron salt, i.e. optionally substituted 1,2-dihalogenbenzene-cyclopentadienyl-iron(II) salt is reacted with an optionally protected piperazine and 2,4-dimethylthiophenol(ate) followed by de-complexation of optionally substituted cyclopentadienyl iron and by de-protection of piperazine as required if protected piperazine is applied in the process to obtain 1-[2-(2,4-dimethyl-phenylsulfanyl)-phenyl]-piperazine. A desired pharmaceutically acceptable salt may be obtained by subsequent reaction with a suitable acid.

Accordingly, in one embodiment the invention provides a process for the manufacture of vortioxetine or pharmaceutically acceptable salts thereof, which process comprises reacting a compound of formula I

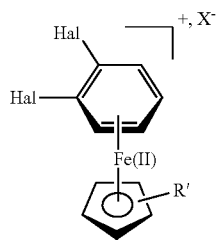

[I]

wherein each Hal independently represents fluoro or chloro; R' represents H or R' represents one or two moieties independently selected from CHO, COOH, COOR''' or COONR$_2$''', or R' represents one to five moieties independently selected from C$_{1-6}$-alkyl; R''' independently represents H or C$_{1-6}$-alkyl; and X$^-$ represents a non-coordinating and non-nucleophilic anion, with an optionally protected piperazine of formula II

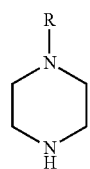

[II]

wherein R represents H or a protective group, and with a compound of formula III

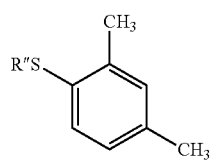

[III]

wherein R'' represents H or a cation and a base as required in a solvent to obtain a compound of formula IV

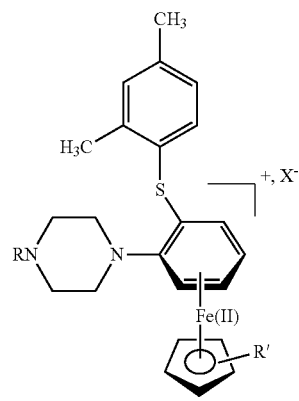

[IV]

followed by a de-complexation step in which the optionally substituted cyclopentadienyliron is de-complexed, and a de-protection step as required in which the optionally protected piperazine moiety is de-protected to obtain 1-[2-(2,4-dimethyl-phenylsulfanyl)-phenyl]-piperazine, i.e. vortioxetine.

The compound of formula I, the compound of formula II and the compound of formula III may be added to the reaction mixture in any sequence or simultaneously.

FIGURES

FIG. 1: Schematic depiction of a flow chemistry set-up for the reaction of the present invention. Compound of formula I is mixed with compound of formula II and compound of formula III to obtain vortioxetine following de-complexation and de-protection as required.

DETAILED DESCRIPTION OF THE INVENTION

The compound of formula I comprises a di-halogen substituted benzene moiety which is η$^6$-bound to the metal centre of a cyclopentadienyl fragment. Said halogen is independently selected from fluoro and chloro. In one embodiment, the halogens are identical; in particular both halogens are chloro. In this embodiment, the di-arene iron compound can be made from very inexpensive starting materials, i.e. 1,2-dichlorobenzene.

R' represents H or R' represents one or two moieties independently selected from CHO, COOH, COOR''' or COONR$_2$''', or R' represents one to five moieties independently selected from C$_{1-6}$-alkyl; R''' independently represents H or C$_{1-6}$-alkyl. In one embodiment, R' represent one C$_{1-6}$-alkyl, such as methyl. In one embodiment, R' is hydrogen, i.e. the cyclopentadienyl moiety is unsubstituted. In one embodiment, R''' represents methyl.

R represents an optional protective group on one of the pipirazine nitrogens. Many protective groups are known in the art, and useful examples include —C(=O)O—W, —C(=O)—W, Boc, Bn and Cbz, and in particular Boc. W represents alkyl or aryl; Bn abbreviates benzyl; Boc abbreviates t-butyloxycarbonyl; and Cbz abbreviates carbobenzyloxy. If a mono-protected piperazine is used in the reaction of the present invention, the protective group has to be removed in a subsequent step, typically by the addition of an acid, such as an aqueous acid. If properly selected, said acid may remove the protective group and provide a desired pharmaceutically acceptable salt of vortioxetine in one and the same step. The use of aqueous HBr may achieve de-protection and the HBr salt of vortioxetine in one step. The reaction of the present invention may run with non-protected piperazine which is beneficial due the reduced number of process steps and thus inherent simplicity.

In the present context, the term "$C_{1-6}$-alkyl" is intended to indicate a straight, branched and/or cyclic saturated hydrocarbon containing 1-6 carbon atoms which alkyl may be substituted. Examples include methyl, ethyl, isopropyl, cyclopentyl and 2-cyclopropyl-ethyl.

In the present context, the term "aryl" is intended to indicate an optionally substituted carbocyclic aromatic hydrocarbon R" represents either hydrogen or a cation which may be either organic or inorganic. Inorganic cation include metal-ion, such as a mono-valent or di-valent metal-ion, such as $K^+$, $Na^+$, $Li^+$ and $Mg^{++}$. Examples of organic cation include 2-hydroxyethyl-trimethylammonium and 1-butyl-3-methylimidazolium. The reaction of the present invention runs best if 2,4-dimethyl thiolate is present. This may be achieved e.g. by adding the thiolate salt (R" represents cation) to the reaction mixture, or by adding the thiophenol compound (R" represents H) and a suitable base as required to obtain the corresponding thio late. A suitable mixture of thiophenol, thio late and a base may also be used. The process of the present invention does not require harsh basic conditions, and bases typically applied in process chemistry may be applied. Examples of useful bases include $K_2CO_3$, NaOEt, NaO(t-Bu), KO(t-Bu), NaOH, KOH and NaH.

$X^-$ represents a non-coordinating and non-nucleophilic anion. In the present context a non-coordinating anion is intended to indicate an anion that essentially does not establish a coordinating bond to the iron in the compound of formula I or formula III. In the present context a non-nucleophilic anion is intended to indicate an anion that essentially does not substitute Hal in the compound of formula I. Typical examples include $BF_4^-$, $PF_6^-$, $ClO_4^-$, $[B[3,5-(CF_3)_2C_6H_3]_4]^-$, $B(C_6F_5)_4^-$ and $Al(OC(CF_3)_3)_4^-$. The use of $PF_6^-$ has the advantage that $PF_6^-$ salts of the compound of formula I are easily isolated and stored. This means that the compound of formula I may be prepared in a process which is separated in time and place from the process of the present invention.

A wide range of solvents may be applied in the process of the present invention. Useful examples include toluene, THF (tetrahydrofuran), MTBE (methyl tert-butyl ether), water, ethanol, 2-propanol, NMP (N-methyl-2-pyrrolidone), DMF (dimethylformamide), MIBK (methylisobutyl ketone), TEA (triethyl amine), DIPEA (N,N-diisopropylethylamine), DCM (dichloromethane), ethylacetate, isopropylacetate and combinations of these.

The optionally substituted cyclopentadienyl-iron fragment is removed in a de-complexation step. This step is well-know from the literature and can be achieved in various ways. *J. Heterocycl. Chem.*, 19, 801-803, 1982 discloses that de-complexation can be achieved by pyrolysis at 200-250° C.; *J. Org Chem*, 67, 5257-5268, 2002 and *J. Polymer. Sci.*, 35, 447-453, 1997 apply photolysis in the presence of $CH_3CN$ and 1,10-phentholine; and *Chem. Soc. Perkin Trans I.*, 197-201, 1994 discloses the use of potassium tert-butoxide at elevated temperatures in high-bioling solvents, such as pyridine or DMSO. Photolysis which is also known as photodissociation or photodecomposition is a chemical reaction where a chemical bond is broken upon irradiation with light. For the reaction of the present invention, de-complexation by photolysis may conveniently be carried out under irradiation with light in the visible or near UV spectrum.

The manufacture of compound of formula I used in the present invention is known from literature. *J. Org. Chem*, 67, 5257-5268, 2002 discloses a process in which 1,2-dichlorobenzene, anhydrous aluminium trichloride, aluminium powder and ferrocene are reacted at 95° C. followed by aqueous work-up and treatment with ammonium hexafluorophosphate. Compounds of formula I where $X^-$ represents a anion different from hexafluorophosphate may be obtained in a similar way by means of a different and appropriate salt, e.g. ammonium $BF_4$. If suitably substituted ferrocene is used, compound of formula I wherein R' is different from H may be obtained.

2,4-Dimethyl-thiophenol, salts thereof and (optionally protected) piperazine are all well-known compounds and readily available in large quantities.

The compound of formula III may for example be obtained from the corresponding arylbromide or arylchloride, i.e. 1-bromo-2,4-dimethyl-benzene or 1-chloro-2,4-dimethyl-benzene in a Grignard-type reaction where said compound is reacted with Mg followed by elemental sulfur to obtain a compound of formula III where R" represent $MgCl^+$ or $MgBr^+$.

An advantage of the process of the present invention is that it runs at low temperature, such as ambient temperature, e.g. 15-30° C. The reaction of the present invention, however, runs both at much higher and much lower temperatures as long as the solvent(s) chosen is sufficiently fluid at the temperature (and pressure) used. In one embodiment, the temperature is between −25° C. and 140° C., such as between 0° C. and 100° C. In one embodiment the temperature is between 10° C. and 80° C., such as 15° C.-50° C.

Pharmaceutically acceptable salts are intended to indicate acid addition salts of acids that are non-toxic. Said salts include salts made from organic acids, such as maleic, fumaric, benzoic, ascorbic, succinic, oxalic, bis-methylene-salicylic, methanesulfonic, ethanedisulfonic, acetic, propionic, tartaric, salicylic, citric, gluconic, lactic, malic, mandelic, cinnamic, citraconic, aspartic, stearic, palmitic, itaconic, glycolic, p-aminobenzoic, glutamic, benzenesulfonic, theophylline acetic acids, as well as the 8-halotheophyllines, for example 8-bromotheophylline. Said salts may also be made from inorganic acids, such as hydrochloric, hydrobromic, sulfuric, sulfamic, phosphoric and nitric acids. Particular mention is made of salts made from hydrobromic acid and lactic acid. Distinct mention is made of the hydrobromide acid salt.

In one embodiment, 1 equivalent of a compound of formula I is mixed with a compound of formula II (1-5 equivalents, such as 1-3 equivalents), a compound of formula III (1-5 equivalents, such as 1-3 equivalents) in a solvent together with a base as needed (more than 0.5 equivalent, such as between 0.5 and 20 equivalents, such as 1-5 equivalents), e.g. at 10-50° C., such as 15-25° C. to obtain a compound of formula IV. The compound of formula IV is then de-complexed, e.g. by photolysis and the protective group on the piperazine is removed as required e.g. by addition of acid to obtain vortioxetine. A pharmaceutically acceptable salt may be obtained by further reaction with an appropriate acid. It may also be feasible to de-protect piperazine as required prior to de-complexation.

In one embodiment, 1 equivalent of a compound of formula I is mixed with a base (more than 0.5 equivalent, such as between 0.5 and 20 equivalents, such as 1-5 equivalents) and piperazine (1-5 equivalents, such as 1-3 equivalents) in a solvent. The mixture is stirred (e.g. at 10-50° C., such as 15-25° C.) and 2,4-dimethyl thiophenol (1-5 equivalents, such as 1-3 equivalents) is added and the reaction is stirred to obtain a compound of formula IV. The compound of formula IV is then de-complexed, e.g. by photolysis to obtain vortioxetine. A pharmaceutically acceptable salt may be obtained by further reaction with an appropriate acid.

In one embodiment, 1 equivalent of $\eta^6$-1,2-dichlorobenzene-$\eta^5$-cyclopenta-dienyliron(II) hexafluorophosphate is mixed with 1-5 equivalent base and piperazine (1-3 equivalent, such as 2 equivalents) in a solvent, such as THF/water. After stirring, 2,4-dimethylthiophenol (1-3 equivalent, such as 2 equivalents) is added and the mixture obtained is stirred to obtain the compound of formula IV, e.g. at 10° C.-50° C. Votioxetine is obtained by de-complexation, e.g. by photolysis.

De-complexation by photolysis may be carried out e.g. in batch mode or in flow mode. De-complexation may conveniently be carried out in the following way. The reaction mixture comprising the compound of formula IV is mixed with aqueous acid (e.g. aqueous HCl) and organic impurities are optionally removed e.g. by addition of an immiscible organic solvent, such as n-heptane, followed by phase separation. The phase containing the compound of formula IV obtained above above is passed through an irradiated glass tube where photolysis occurs to obtain vortioxetine. As an example, the aqueous phase may be circulated through an irradiated glass tube.

Alternatively, the compound of formula I may be prepared and used immediately in the process of the present invention without isolation. For example 1,2-dichlorobenzene (2-20 equivalents, such as 3-6 equivalents) is mixed with a suitably substituted ferrocene (1 equivalent), aluminium chloride (0.1-2 equivalent, such as 0.2-1 equivalent) and fine aluminium powder (0.01-0.5 equivalent, such as 0.05-0.2 equivalent) and heated to 80-120°, such as 100-110° to obtain a compound of formula I. The compound of formula I may then be further reacted as described above to obtain vortioxetine.

The process of the present invention may be run in batch mode, wherein the reactants are added to a vessel or container. Alternatively, the process of the present invention is amenable to flow chemistry wherein the reactants are mixed and pumped through tubes wherein the reaction takes place. FIG. 1 depicts a schematic flow set-up for the reaction of the present invention. The reaction of the present invention may also be carried out partly in batch mode and partly in a flow set-up.

In one embodiment, the invention relates to vortioxetine and pharmaceutically acceptable salts thereof manufactured by a process of the present invention.

As demonstrated in the examples, the present invention provides a non-resin based manufacturing process for vortioxetine and pharmaceutically acceptable salts thereof in which an asymmetric displacement of two identical halogen atoms from a symmetric reactant (1,2-dihalogenbenzene) is effected in a one-pot synthesis, i.e. without the need for isolation of intermediates, such as intermediates where only one halogen is substituted. The process of the present invention avoids the use of expensive reactants and catalysts; it can be run at low temperatures and generally at mild conditions. Thus, simple and inexpensive manufacturing equipment can be applied, and the risk of unwanted side-reactions is minimized. High yields and high purity are achieved, and the process of the present invention is well-suited for industrial scale.

All references, including publications, patent applications, and patents, cited herein are hereby incorporated by reference in their entirety and to the same extent as if each reference were individually and specifically indicated to be incorporated by reference and were set forth in its entirety herein, regardless of any separately provided incorporation of particular documents made elsewhere herein.

The use of the terms "a" and "an" and "the" and similar referents in the context of describing the invention are to be construed to cover both the singular and the plural, unless otherwise indicated herein or clearly contradicted by context. For example, the phrase "the compound" is to be understood as referring to various compounds of the invention or particular described aspect, unless otherwise indicated.

The description herein of any aspect or aspect of the invention using terms such as "comprising", "having," "including," or "containing" with reference to an element or elements is intended to provide support for a similar aspect or aspect of the invention that "consists of", "consists essentially of", or "substantially comprises" that particular element or elements, unless otherwise stated or clearly contradicted by context (e.g., a composition described herein as comprising a particular element should be understood as also describing a composition consisting of that element, unless otherwise stated or clearly contradicted by context).

EXAMPLES

Example 1

$\eta^6$-1,2-Dichlorobenzene-$\eta^5$-cyclopentadienyliron(II) hexafluorophosphate (25 g, 61 mmol), potassium carbonate (16.7 g, 121 mmol) and piperazine (10.3 g, 120 mmol) was dissolved in a mixture of THF (200 mL) and water (50 mL). The reaction mixture was stirred for 1 h at ambient temperature. To the reaction mixture was added 2,4-dimethyl thiophenol (8.8 g, 63.7 mmol) and stirring was continued overnight.

The reaction mixture was poured into aqueous hydrochloric acid (2 M, 200 mL) over a period of 20 min. To the mixture was added n-heptane (15 mL) and the phases were separated. The organic phase was extracted once with water (15 mL). The THF/water phase was circulated at room temperature through an irradiated glass spiral (100 W incandescent light). During this step water and THF separated and only the lower water phase was pumped through the photolysis equipment, and the liberated 1-[2-(2,4-dimethyl-phenylsulfanyl)-phenyl]-piperazine concentrated in the upper THF phase.

After complete de-complexation, the phases were separated and the water phase was extracted twice with THF (2×70 mL). The combined THF phases were diluted with toluene (50 mL) and subsequently washed twice with aqueous sodium hydroxide solution (1.0 M, 50 mL and 30 mL).

The organic phase was separated, and the THF was removed at 40° C. at reduced pressure. The resulting solution was added slowly to a mixture of aqueous hydrobromic acid (48 w/w %, 7.0 mL, 62 mmol), water (20 mL) and toluene (10 mL) at 40° C. The desired 1-[2-(2,4-dimethyl-phenylsulfanyl)-phenyl]-piperazine HBr was isolated by filtration. The filter cake was washed with toluene (40 mL) and water (10 mL) yielding 1-[2-(2,4-dimethyl-phenylsulfanyl)-phenyl]-piperazine HBr (13.3 g, 35.0 mmol 64.1%) as a white powder.

Al 1 ppm, Fe 401 ppm, Na 291 ppm, P 2453 ppm (as determined by ICP-AES).

Purity: Area %: Vortioxetine 99.73, 1-[2-(3,5-dimethyl-phenylsulfanyl)-phenyl]-piperazine 0.08%, unknowns 0.19 (as determined by GC).

$^1$H NMR (DMSO-d6): 8.84 (bs, 2H), 7.34 (d, 1H, 7.7 hz), 7.26 (s, 1H), 7.16 (m, 2H), 7.11 (dd, 1H, 7.8 and 1.7 hz), 6.97 (dd, 1H, 7.8 and 1.7 hz), 6.41 (dd, 1H, 7.8 and 1.3 hz), 3.26 (bm, 4H), 3.20 (bm, 4 H), 2.33 (s, 3H), 2.25 (s, 3H).

Crystal form: β-form (as determined by XRPD). Please see WO 2007/144005 for definition of the α-form and β-form of vortioxetine HBr.

Water content: <0.1% (as determined by Karl Fisher) and <0.2% (as determined by thermo gravimetric analysis).

Elemental analysis $C_{18}H_{23}N_2SBr$ requires C, 56.99; H, 6.11; N, 7.38. found C, 57.10; H, 6.12; N, 7.26.

Example 2

1,2-Dichloro benzene (158.4 g, 1.08 mol), ferrocene (40.6 g, 218 mmol), aluminium trichloride (13.8 g, 104 mmol) and fine aluminium powder (7.0 g, 26 mmol) were mixed and heated at 110° C. for 6 h. The reaction mixture was cooled to 25° C. and added slowly to a mixture of ice (240 g) and n-heptane (100 mL) over 25 minutes. (CAUTION: the treatment of unreacted aluminium trichloride with water is highly exothermic).

The mixture was treated with Celite 545® (14 g) and stirred at ambient temperature for 20 minutes prior to filtration. The filter cake was washed with water (15 mL). The filtrates were combined, and the phases were separated. The water phase was washed with toluene (2×50 mL). To the water phase was slowly added aqueous sodium hydroxide (10.8 M, 70 mL, 0.76 mol) until the pH was 6.5. The precipitated aluminium oxides was removed by filtration, and the filter cake was washed with water (25 mL).

The collected aqueous phases was added to a mixture of potassium carbonate (20 g, 0.14 mol) and piperazine (9.4 g, 0.11 mol) in THF (100 mL) and stirred for 3 hours at ambient temperature. To this mixture was added 2,4-dimethyl thiophenol (8.9 g, 64 mmol) and stirring was continued overnight.

The reaction mixture was poured slowly into aqueous hydrochloride acid (4.0 M, 130 mL, 0.52 mol). The reaction mixture was pumped through an irradiated glass tube (100 W incandescent light). During this step water and THF separated and only the lower water phase was pumped through the photolysis equipment, and the liberated 1-[2-(2,4-dimethyl-phenylsulfanyl)-phenyl]-piperazine concentrated in the upper THF phase.

After de-complexation was completed, the phases were separated and the water phase was extracted twice with toluene (2 ×70 mL). The combined organic phases were washed with sodium hydroxide (1.0 M, 70 mL, 70 mmol) and then with water (25 mL). The THF was removed at 40° C. at reduced pressure. The toluene solution was added slowly to a mixture of aqueous hydrobromic acid (48 w/w %, 7.5 mL, 67 mmol), water (20 mL) and toluene (10 mL) at 35° C. 1-[2-(2, 4-Dimethyl-phenylsulfanyl)-phenyl]-piperazine HBr was isolated by filtration. The filter cake was washed with toluene (40 mL) and water (10 mL) yielding 1-[2-(2,4-dimethyl-phenylsulfanyl)-phenyl]-piperazine HBr (7.3 g, 19.2 mmol, 8.8% from ferrocene) as an off-white powder.

Al 6 ppm, Fe 18 ppm, Na 3 ppm, P 7 ppm (as determined by ICP-AES)

Purity: Area %: Vortioxetine 99.96, 1-[2-(3,5-dimethyl-phenylsulfanyl)-phenyl]-piperazine 0.04, unknown 0% (as determined by GC)

$^1$H NMR (DMSO-d6): 8.86 (bs, 2H), 7.34 (d, 1H, 7.7 hz), 7.26 (s, 1H), 7.16 (m, 2H), 7.11 (d, 1H, 7.9), 6.97 (dd, 1H, 7.8 and 1.8 hz), 6.41 (dd, 1H, 7.7 and 1.4 hz), 3.27 (bm, 4H), 3.21 (bm, 4 H), 2.33 (s, 3H), 2.25 (s, 3H).

Crystal form: Mixture of α and β-form (as determined by XRPD).

Water content: 0.14% (as determined by Karl Fisher) and <0.2% (as determined by thermo gravimetric analysis).

Elemental analysis $C_{18}H_{23}N_2SBr$ requires C, 56.99; H, 6.11; N, 7.38. found C, 56.94; H, 6.09; N, 7.31.

The invention claimed is:

1. A process for the manufacture of vortioxetine or pharmaceutically acceptable salts thereof, which process comprises reacting a compound of formula I

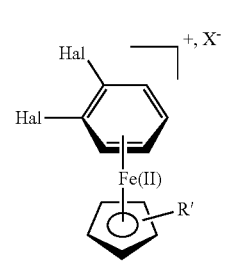

[I]

wherein each Hal independently represents fluoro or chloro; R' represents H or R' represents one or two moieties independently selected from CHO, COOH, COOR''' or COONR'''$_2$, or R' represents one to five moieties independently selected from C$_{1-6}$-alkyl; R''' independently represents H or C$_{1-6}$-alkyl; and X$^-$ represents a non-coordinating and non-nucleophilic anion, with a piperazine of formula II

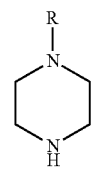

[II]

wherein R represents H,
and with a compound of formula III

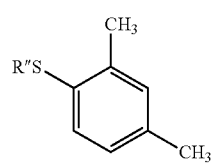

[III]

wherein R" represents H or a cation, and an optional base in a solvent to obtain a compound of formula IV

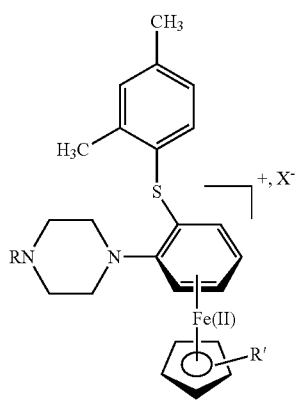

followed by a de-complexation step in which the optionally substituted cyclopentadienyliron is de-complexed to obtain 1-[2-(2,4-dimethyl-phenylsulfanyl)-phenyl]-piperazine (vortioxetine).

2. The process according to claim 1, wherein Hal represents chloro.

3. The process according to claim 1, wherein R' represents hydrogen.

4. The process according to claim 1, wherein X⁻ is selected from the group consisting of $PF_6^-$, $AlCl_4^-$, $ClO_4^-$, $BF_4^-$, $[B[3,5-(CF_3)_2C_6H_3]_4]^-$, $B(C_6F_5)_4^-$ and $Al(OC(CF_3)_3)_4^-$.

5. The process according to claim 4, wherein X⁻ is $PF_6^-$.

6. The process according to claim 1, wherein said solvent is selected from the group consisting of toluene, THF (tetrahydrofuran), MTBE (methyl tertiary-butyl ether), water, ethanol, 2-propanol, NMP (N-Methyl-2-pyrrolidone), DMF (dimethylformamide), MIBK (methylisobutyl ketone), TEA (triethyl amine), DIPEA (N,N-diisopropylethylamine), DCM (dichloromethane), ethylacetate, isopropylacetate and combinations of these.

7. The process according to claim 1, wherein R" represents H.

8. The process according to claim 1, wherein said de-complexation step comprises photolysis.

9. The process according to claim 1, wherein 1 equivalent of a compound of formula I is mixed with a compound of formula II (1-5 equivalents) and a compound of formula III (1-5 equivalents) in a solvent together with a base (more than 0.5 equivalent) to obtain a compound of formula IV followed by de-complexation to obtain 1-[2-(2,4-dimethyl-phenylsulfanyl)-phenyl]-piperazine.

10. The process according to claim 1, wherein 1 equivalent of a compound of compound of formula I is mixed with a base (between 0.5 and 20 equivalents), piperazine (1-5 equivalents) and 2,4-dimethyl thiophenol (1-5 equivalents) in a solvent to obtain a compound of formula IV, followed by de-complexation to obtain 1-[2-(2,4-dimethyl-phenylsulfanyl)-phenyl]-piperazine.

11. The process according to claim 1, wherein 1 equivalent of $\eta^6$-1,2-dichlorobenzene-$\eta^5$-cyclopentadienyliron(II) hexafluorophosphate is mixed with 1-5 equivalent base, 1-3 equivalents 2,4-dimethylthiophenol and 1-3 equivalents piperazine in a solvent at 10° C-50° C. to obtain the compound of the formula

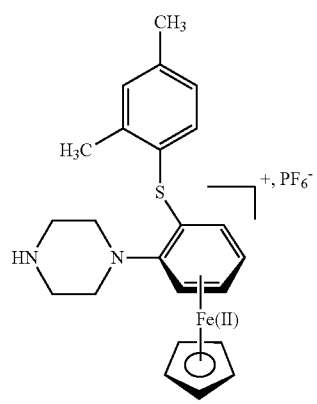

followed by de-complexation to obtain 1-[2-(2,4-dimethyl-phenylsulfanyl)-phenyl]-piperazine.

12. The process according to claim 1, wherein the obtained 1-[2-(2,4-dimethyl-phenylsulfanyl)-phenyl]-piperazine is reacted with a suitable acid to obtain the equivalent pharmaceutically acceptable salt.

* * * * *